(12) United States Patent
Cho et al.

(10) Patent No.: US 6,893,493 B2
(45) Date of Patent: May 17, 2005

(54) PREPARATION METHOD OF SOLVENT-FREE WATER-DISPERSIBLE HYDROXYPROPYL METHYL CELLULOSE PHTHALATE NANOPARTICLE

(75) Inventors: Kyu-Il Cho, Daejeon (KR); Hyon-Ho Baek, Daejeon (KR); Jung Hyun Kim, Seoul (KR); Jun Young Lee, Seoul (KR); Il Hyuk Kim, Seoul (KR); Jung Hwan Park, Kyunggi-do (KR)

(73) Assignee: Samsung Fine Chemicals Co., Ltd., Ulsan (KR)

(*) Notice: Subject to any disclaimer, the term of this patent is extended or adjusted under 35 U.S.C. 154(b) by 62 days.

(21) Appl. No.: 10/250,790

(22) PCT Filed: Nov. 22, 2001

(86) PCT No.: PCT/KR01/02015

§ 371 (c)(1),
(2), (4) Date: Jul. 9, 2003

(87) PCT Pub. No.: WO03/042248

PCT Pub. Date: May 22, 2003

(65) Prior Publication Data

US 2005/0000388 A1 Jan. 6, 2005

(30) Foreign Application Priority Data

Nov. 15, 2001 (KR) .......................................... 2001-70966

(51) Int. Cl.[7] .......................... C08L 1/28; C09D 101/28
(52) U.S. Cl. .............................. 106/169.01; 106/170.5; 106/170.51; 106/170.34
(58) Field of Search ....................... 106/169.01, 170.34, 106/170.5, 170.51

(56) References Cited

U.S. PATENT DOCUMENTS

| 5,512,092 A | * | 4/1996 | Maruyama et al. | .... 106/168.01 |
| 5,560,930 A | * | 10/1996 | Maruyama et al. | ......... 424/488 |
| 5,851,579 A | * | 12/1998 | Wu et al. | ................ 427/2.21 |

FOREIGN PATENT DOCUMENTS

| EP | 0648 487 A1 | 4/1995 |
| JP | 57-62224 | 4/1982 |
| JP | 58-55413 | 4/1983 |
| JP | 10-7558 | 1/1998 |
| KR | 2000-0010730 | 2/2000 |

* cited by examiner

*Primary Examiner*—David Brunsman
(74) *Attorney, Agent, or Firm*—Finnegan, Henderson, Farabow, Garrett & Dunner, LLP

(57) ABSTRACT

The present invention relates to a preparation method of solvent-free water-dispersible hydroxypropyl methyl cellulose phthalate nanoparticle, and more particularly, to a preparation method of solvent-free water-dispersible hydroxypropyl methyl cellulose phthalate nanoparticle, which is environment-friendly and advantageous in disintegration and dissolution when used as an enteric coating material, which is prepared by obtaining suitable hydroxypropyl methyl cellulose phthalate (HPMCP) particle through aqueous emulsification process and regulating content of remaining electrolyte through ion exchange process.

7 Claims, No Drawings

PREPARATION METHOD OF SOLVENT-FREE WATER-DISPERSIBLE HYDROXYPROPYL METHYL CELLULOSE PHTHALATE NANOPARTICLE

CROSS REFERENCE TO RELATED APPLICATIONS

This application is a national phase of international application number PCT/KR01/02015, filed Nov. 22, 2001, the content of which is incorporated herein by reference and claims the priority of Korean Patent Application No. 2001/70966, filed Nov. 15, 2001.

FIELD OF THE INVENTION

The present invention relates to a preparation method of solvent-free water-dispersible hydroxypropyl methyl cellulose phthalate nanoparticle, and more particularly, to a preparation method of solvent-free water-dispersible hydroxypropyl methyl cellulose phthalate nanoparticle, which is environment-friendly and advantageous in disintegration and dissolution when used as an enteric coating material, which is prepared by obtaining suitable hydroxypropyl methyl cellulose phthalate (HPMCP) particle through aqueous emulsification process and regulating content of remaining electrolyte through ion exchange process.

Until now, mainly hydroxypropyl methyl cellulose phthalate and acrylate have been used as enteric coating materials. However, for hydroxypropyl methyl cellulose phthalate, organic solvent is used during coating process, which may cause environmental problem. And, for acrylate, although the water-dispersible product is available, it is a synthetic polymer rather than a natural material and it has poor film properties compared to those of hydroxypropyl methyl cellulose phthalate. Therefore, need of a new type of environment-friendly material has been increased.

In this regard, water-dispersible hydroxypropyl methyl cellulose phthalate has been prepared. The conventional method of preparing this water-dispersible hydroxypropyl methyl cellulose phthalate comprises: completely dissolving hydroxypropyl methyl cellulose phthalate with organic solvent and dispersing it in water; removing organic solvent in the solution to obtain water-dispersible type of hydroxypropyl methyl cellulose phthalate. However, the product obtained by this method has poor stability in water-dispersible phase. Further, the use of an organic solvent incurs an increase in manufacturing cost, and it also has a drawback that the organic solvent is hardly removed from the final product thereby causing an environmental problem.

U.S. Pat. No. 5,560,930 discloses a method of preparing particle of about 0.2% by emulsifying hydroxypropyl methyl cellulose phthalate in water after dissolving it in acetone and removing the organic solvent through distillation under reduced pressure. It discloses examples of using a solvent mixture, such as ethanol/water and methanol/water. U.S. Pat. No. 5,512,092 discloses a method of dissolving hydroxypropyl methyl cellulose phthalate in ethanol and emulsifying it; and U.S. Pat. No. 5,346,542 discloses a method of dissolving carboxymethyl ethyl cellulose in methyl acetate and emulsifying it in water. Although these methods do not have problems of latex particle size or dispersion, product stability after emulsification is poor and leaves the organic solvent in the final product because it is difficult to remove organic solvent remaining in the solution. We prepared water-dispersible hydroxypropyl methyl cellulose phthalate according to the above method in 1 cm×1 cm film. When it was placed in aqueous solution of pH 1.2 for 2 hr, the film was dissolved. And, we diluted this water-dispersible hydroxypropyl methyl cellulose phthalate to 7 wt % with distilled water and coated it on the tablet using Hi-Coater (HCT Labo, Freund Co.). The disintegration test (Pharmatest PTZ E) showed that disintegration took place in 2 hr under pH 1.2. Because of this, commercialization of water-dispersible hydroxypropyl methyl cellulose phthalate has not been achieved as yet.

SUMMARY OF THE INVENTION

In order to solve these problems, we prepared stable particles by introducing aqueous emulsification process of hydroxypropyl methyl cellulose phthalate (HPMCP) without using an organic solvent. And, we regulated the amount of remaining electrolytes through ion exchange process in order to obtain hydroxypropyl methyl cellulose phthalate.

Accordingly, an object of the present invention is to provide a preparation method of solvent-free water-dispersible hydroxypropyl methyl cellulose phthalate nanoparticle, which is environment-friendly and advantageous in disintegration and dissolution without having the problem of leaving the organic solvent in the final product.

DETAILED DESCRIPTION OF THE INVENTION

The present invention is characterized by a preparation method of solvent-free water-dispersible hydroxypropyl methyl cellulose phthalate nanoparticles, which comprises:

1) a step of emulsifying hydroxypropyl methyl cellulose phthalate at 20–70° C. for 4–6 hr using emulsifying agent and $NH_4OH$; and 2) an ion exchange step of reducing content of electrolyte remaining in hydroxypropyl methyl cellulose phthalate obtained by the step 1) to 050 mS using ion exchange resin or membrane.

Hereunder is given a detailed description of the present invention.

The present invention is characterized by a preparation method of water-dispersible hydroxypropyl methyl cellulose phthalate nanoparticle stable in water, by neutralizing a phthalate group of hydroxypropyl methyl cellulose phthalate with $NH_4OH$ and controlling electrolyte content remaining in the solution through ion exchange process.

Hereunder is given a more detailed description of the present invention.

Firstly, the step 1 is a step of forming water-stable particle by emulsifying hydroxypropyl methyl cellulose phthalate at 20–70° C. for 4–6 hr using an emulsifying agent and $NH_4OH$. For hydroxypropyl methyl cellulose phthalate, the one with 40,000–60,000 of mean molecular weight can be used. And as an emulsifying agent, Pluronic F-68, Triton X-405, Tween-80, Polystep B-1 or Polystep F-9 can be used. The emulsifying agent is preferred to be used in 0.05–1.0 wt % against hydroxypropyl methyl cellulose phthalate. If its content is below 0.05 wt %, stability of water-stable HPMCP is deteriorated; and if it exceeds 1.0 wt %, film property is lowered when it is coated on tablet. For neutralizer, $NH_4OH$ can be used. Its content is preferred to be 1.6–4.0 wt % against hydroxypropyl methyl cellulose phthalate. If it is below 1.6 wt %, there can arise a stability problem because particle size is enlarged; and if it exceeds 4.0 wt %, the tablet may give off ammonia-like odor due to excess use of $NH_4OH$. In particular, it is preferred to use 28% $NH_4OH$ solution.

The step 2 is an ion exchange step to regulate remaining electrolyte content to 0–50 mS by using ion exchange resin or membrane. If the remaining electrolyte content is above this range, excess amount of ion exchange resin has to be used to remove the remaining electrolyte. For ion exchange resin, cation exchange resin, e.g., Dowex MR-3 (Sigma-Aldrich, US) can be used. For membrane, it is recommended to use the one with pores of 100–300 nm in size. If the pore size is below 100 nm, a considerable amount of time is required to remove remaining electrolyte; and if it exceeds 300 nm, the HPMCP particle may penetrate the membrane, which may cause reduction of solid content. Here, the remaining electrolyte means the ammonium ion which forms salt, and it affects physical properties of hydroxypropyl methyl cellulose phthalate.

The present invention includes water-dispersible hydroxypropyl methyl cellulose phthalate prepared by said steps 1 and 2. The obtained water-dispersible hydroxypropyl methyl cellulose phthalate has 100–1000 nm of particle size and contains 7–30 wt % of solid contents.

The hydroxypropyl methyl cellulose phthalate prepared by the present invention shows no particle sedimentation when stored for long time in water and does not dissolve in pH 1.2 when it is coated on tablet. Therefore, it can be used as environment-friendly enteric coating material.

The following examples are intended to be illustrative of the present invention, and they should not be construed as limiting the scope of this invention.

EXAMPLE 1

400 g of distilled water, 1.0 g of Pluronic F-68 and 100 g of hydroxypropyl methyl cellulose phthalate (Mw 40,000–60,000, Samsung Fine Chemicals Co., Ltd. Brand name with AnyCoat-P) were placed in 1L reactor equipped with a stirrer and stirred at 300–350 rpm. 28%-$NH_4OH$ (8 g) was slowly added to this solution and the temperature was raised to 60° C. After stirring for another 4–5 hr while maintaining the temperature, the remaining ammonium ion concentration was regulated to 0.0–7 mS using ion exchange resin [Dowex MR-3, Sigma-Aldrich, US].

The prepared water-dispersible hydroxypropyl methyl cellulose phthalate had 4.6±1.0 of pH, 25±5% of solid content, 140±5 of acid value and 300±50 nm of particle size.

The pH was measured with a pH meter of Orion research, Inc. and the solid content was measured by gravimetric determination. The acid value represents distribution of a carboxyl group per unit surface area. 0.1 N KOH was used to determine the acid value; and THF and methanol were used to dissolve dry sample. The particle size was measured by dynamic light scattering (DLS; Zetaplus, Brookhaven Instruments).

The obtained water-dispersible hydroxypropyl methyl cellulose phthalate was made into 1 cm×1 cm film and placed in pH 1.2 of an aqueous solution. When it was taken out after 2 hr, it remained in shape without being dissolved. The water-dispersible hydroxypropyl methyl cellulose phthalate was diluted to 7 wt % with distilled water and coated on tablet using Hi-Coater (HCT Labo) The disintegration test (Pharmatest PTZ E) showed that no disintegration took place for 2 hr under pH 1.2.

EXAMPLE 2

400 g of distilled water, 0.53 g of Triton X405 and 106 g of hydroxypropyl methyl cellulose phthalate (Mw 40,000–60,000, Samsung Fine Chemicals Co., Ltd.) were put in 1L reactor equipped with a stirrer and stirred at 300–350 rpm at room temperature. 28%-$NH_4OH$ (10 g) was slowly added to this solution and it was stirred for another 4–5 hr. The remaining ammonium ion concentration was regulated to 0.0–7 mS using ion exchange resin [Dowex MR-3, Sigma-Aldrich, US].

The prepared water-dispersible hydroxypropyl methyl cellulose phthalate had 4.8±1.0 of pH, 19.9% of solid content, 145 of acid value and 700:50 nm of particle size.

The obtained water-dispersible hydroxypropyl methyl cellulose phthalate was made into 1 cm×1 cm film and put in pH 1.2 of an aqueous solution. When it was taken out after 2 hr, it remained in shape without being dissolved. The water-dispersible hydroxypropyl methyl cellulose phthalate was diluted to 7 wt % with distilled water and coated on a tablet using Hi-Coater (HCT Labo). The disintegration test (Pharmatest PTZ E) showed that no disintegration took place in 2 hr under pH 1.2.

EXAMPLE 3

400 g of distilled water, 0.7 g of Polystep B-1 and 100 g of hydroxypropyl methyl cellulose phthalate (Mw 40,000–60,000, Samsung Fine Chemicals Co., Ltd.) were placed in a 1L reactor equipped with a stirrer and stirred at 300–350 rpm at room temperature. 28%-$NH_4OH$ (11.5 g) was slowly added to this solution and it was stirred for another 4–5 hr. The remaining ammonium ion concentration was adjusted to 0.0–7 mS using membrane (pore size: 200 nm). Because emulsifying agent is removed together with the remaining ammonium ion, the emulsifying agent was replenished continuously so as not to alter the emulsifying agent concentration.

The prepared water-dispersible hydroxypropyl methyl cellulose phthalate had 8 ±0.5 of pH, 20.0% of solid content, 140 of acid value and 100±50 nm of particle size.

The obtained water-dispersible hydroxypropyl methyl cellulose phthalate was made into 1 cm×1 cm film and placed in pH 1.2 of an aqueous solution. When it was taken out after 2 hr, it remained in shape without being dissolved. The water-dispersible hydroxypropyl methyl cellulose phthalate was diluted to 7 wt % with distilled water and coated on tablet using Hi-Coater (HCT Labo). The disintegration test (Pharmatest PTZ E) showed that no disintegration took place in 2 hr under pH 1.2.

EXAMPLE 4

400 g of distilled water, 0.5 g of Tween-80 and 100 g of hydroxypropyl methyl cellulose phthalate (Mw 40,000–60,000, Samsung Fine Chemicals Co., Ltd.) were placed in a 1L reactor equipped with a stirrer and stirred at 300–350 rpm. 28%-$NH_4OH$ (8 g) was slowly added to this solution and the temperature was raised to 60° C. After stirring for another 4–5 hr while maintaining the temperature, the remaining ammonium ion concentration was adjusted to 0.0–7 mS using ion exchange resin (Dowex MR-3, Sigma-Aldrich, US).

The prepared water-dispersible hydroxypropyl methyl cellulose phthalate had 4.6±1.0 of pH, 25±5% of solid content, 140±5 of acid value and 500±50 nm of particle size.

The obtained water-dispersible hydroxypropyl methyl cellulose phthalate was made into 1 cm×1 cm film and placed in pH 1.2 of an aqueous solution. When it was taken out after 2 hr, it remained in shape without being dissolved. The water-dispersible hydroxypropyl methyl cellulose phthalate was diluted to 7 wt % with distilled water and coated on a tablet using Hi-Coater (HCT Labo). The disintegration test (Pharmatest PTZ E) showed that no disintegration took place in 2 hr under pH 1.2.

EXAMPLE 5

400 g of distilled water, 0.65 g of Polystep F-9 and 106 g of hydroxypropyl methyl cellulose phthalate (Mw 40,000–60,000, Samsung Fine Chemicals Co., Ltd.) were placed in a 1L reactor equipped with a stirrer and stirred at 300–350 rpm at room temperature. 28%-$NH_4OH$ (10 g) was slowly added to this solution and it was stirred for another 4–5 hr. The remaining ammonium ion concentration was adjusted to 0.0–7 mS using ion exchange resin (Dowex MR-3; Sigma-Aldrich, US).

The prepared water-dispersible hydroxypropyl methyl cellulose phthalate had 4.8±1.0 of pH, 19.9% of solid content, 145 of acid value and 200±50 mm of particle size.

The obtained water-dispersible hydroxypropyl methyl cellulose phthalate was made into 1 cm×1 cm film and put in pH 1.2 aqueous solution. When it was taken out after 2 hr, it remained in shape without being dissolved. The water-dispersible hydroxypropyl methyl cellulose phthalate was diluted to 7 wt % with distilled water and coated on a tablet using Hi-Coater (HCT Labo). The disintegration test (Pharmatest PTZ E) showed that no disintegration took place for 2 hr under pH 1.2.

COMPARATIVE EXAMPLE 1

U.S. Pat. No. 5,560,930 discloses the following method. 0.3 kg of hydroxypropyl methyl cellulose phthalate dissolved in 9.7 kg of acetone is emulsified in 10 kg of distilled water while stirring at 100 rpm. The prepared emulsion is distilled under reduced pressure under the condition of 50° C./−590 mm to remove an organic solvent.

However, when we followed this procedure, although there was no problem of latex particle size or dispersion, there was a problem of product stability after emulsification and it was difficult to remove the organic solvent. Especially, the organic solvent remained in the final product. We also made 1 cm×1 cm film with the obtained water-dispersible hydroxypropyl methyl cellulose phthalate and put in pH 1.2 of an aqueous solution. When it was taken out after 2 hr, the film had been dissolved. Also, we diluted the water-dispersible hydroxypropyl methyl cellulose phthalate to 7 wt % with distilled water and coated it on a tablet using Hi-Coater (HCT Labo). The disintegration test (Pharmatest PTZ E) showed that disintegration took place for 2 hr under pH 1.2.

As explained above, the present invention provides a new type of preparation method of water-dispersible hydroxypropyl methyl cellulose phthalate nanoparticle by preparing stable particle through introduction of aqueous emulsification process and regulating remaining electrolyte content through ion exchange process. As a result, the present invention resolves the environmental problem of the conventional method using organic solvent while maintaining basic properties of hydroxypropyl methyl cellulose phthalate. Therefore, it can be used as a new concept for environment-friendly enteric coating material.

What is claimed is:

1. A preparation method of solvent-free water-dispersible hydroxypropyl methyl cellulose phthalate nanoparticle comprising the steps of:
   1) emulsifying hydroxypropyl methyl cellulose using an emulsifying agent and $NH_4OH$; and
   2) regulating the remaining electrolyte content to 0–50 mS using ion exchange resin or membrane.

2. The preparation method of solvent-free water-dispersible hydroxypropyl methyl cellulose phthalate nanoparticle according to claim 1, wherein said step 1) is carried out at a temperature ranging from 20–70° C.

3. The preparation method of solvent-free water-dispersible hydroxypropyl methyl cellulose phthalate nanoparticle according to claim 1, wherein said step 1) is carried out for 4–6 hours.

4. The preparation method of solvent-free water-dispersible hydroxypropyl methyl cellulose phthalate nanoparticle according to claim 1, wherein the content of said emulsifying agent and $NH_{40}OH$ in step 1) is 0.05–1.0 wt % and 1.6–4.0 wt % against hydroxypropyl methyl cellulose phthalate, respectively.

5. The preparation method of solvent-free water-dispersible hydroxypropyl methyl cellulose phthalate nanoparticle according to claim 1, wherein said ion exchange resin in step 2) is cation exchange resin and said membrane has pores of 100–300 nm in size.

6. A water-dispersible hydroxypropyl methyl cellulose phthalate prepared by the preparation method according to claim 1.

7. The water-dispersible hydroxypropyl methyl cellulose phthalate according to claim 6, which has 100–1000 nm of particle size and 7–30 wt % of solids content.

\* \* \* \* \*

UNITED STATES PATENT AND TRADEMARK OFFICE
CERTIFICATE OF CORRECTION

PATENT NO. : 6,893,493 B2
DATED : November 30, 2004
INVENTOR(S) : Kyu-II Cho et al.

It is certified that error appears in the above-identified patent and that said Letters Patent is hereby corrected as shown below:

Column 6,
Line 31, "$NH_{40}OH$" should read -- $NH_4OH$ --.

Signed and Sealed this

Nineteenth Day of July, 2005

JON W. DUDAS
*Director of the United States Patent and Trademark Office*